United States Patent
Kump et al.

(10) Patent No.: US 6,795,526 B2
(45) Date of Patent: Sep. 21, 2004

(54) AUTOMATIC EXPOSURE CONTROL FOR A DIGITAL IMAGE ACQUISITION SYSTEM

(75) Inventors: Kenneth S. Kump, Waukesha, WI (US); Francois S. Nicolas, Gif sur Yvette (FR); Christopher D. Unger, Delafield, WI (US); Matthew J. Walker, New Berlin, WI (US)

(73) Assignee: GE Medical Systems Global Technology Co., LLC, Waukesha, WI (US)

( * ) Notice: Subject to any disclaimer, the term of this patent is extended or adjusted under 35 U.S.C. 154(b) by 199 days.

(21) Appl. No.: 09/683,927

(22) Filed: Mar. 4, 2002

(65) Prior Publication Data

US 2003/0165216 A1 Sep. 4, 2003

(51) Int. Cl.[7] .................................................. H05G 1/26
(52) U.S. Cl. ......................................... 378/116; 378/95
(58) Field of Search ............................ 378/108, 95–97, 378/115, 98.12, 116

(56) References Cited

U.S. PATENT DOCUMENTS

| | | | |
|---|---|---|---|
| 5,164,583 A | 11/1992 | Aichinger et al. | |
| 5,574,764 A | 11/1996 | Granfors et al. | |
| 6,047,042 A | 4/2000 | Khutoryansky et al. | |
| 6,118,892 A | 9/2000 | Williams | |
| 6,233,473 B1 * | 5/2001 | Shepherd et al. | 600/407 |
| 6,325,537 B1 * | 12/2001 | Watanabe | 378/197 |
| 6,459,765 B1 * | 10/2002 | Ganin et al. | 378/108 |

* cited by examiner

Primary Examiner—Edward J. Glick
Assistant Examiner—Hoon Song
(74) Attorney, Agent, or Firm—Peter J. Vogel (57) ABSTRACT

A method and system for of defining, or identifying, regions of interest for exposure management in a digital x-ray imaging system, and especially in the case of multiple consecutive image acquisitions. According to the most basic embodiment of the present invention, simple geometric shapes arranged in a matrix configuration are used to aid an operator in identifying a region of interest for a diagnostic x-ray image. Each region of interest is selectable from a low-dose preshot image and may be corrected, or processed, in order to enhance the results of a subsequent diagnostic image. The processing of the preshot image allows the system to automatically make predictions for the diagnostic image exposure requirements, thereby avoiding unnecessary multiple images.

32 Claims, 6 Drawing Sheets

| System Geometry Value | ROI Shape Before Geometry Value Change | ROI Shape After Geometry Value Increase | ROI Shape After Geometry Value Decrease | Type of Geometrical Transformation on ROI |
|---|---|---|---|---|
| SID [mm] | □ | □ (larger) | □ (smaller) | Uniform Dilation |
| Tube Angle (Lateral) [°] | □ | trapezoid (wide top) | trapezoid (wide bottom) | Non-uniform Dilation |
| Tube Angle (Longitudinal) [°] | □ | trapezoid (wide right) | trapezoid (wide left) | Non-uniform Dilation |
| Detector Angle (Lateral) [°] | □ | trapezoid (wide bottom) | trapezoid (wide top) | Non-uniform Dilation |
| Detector Angle (Longitudinal) [°] | □ | trapezoid (wide left) | trapezoid (wide right) | Non-uniform Dilation |
| Collimator FOV [mm] | □ | □ (wider) | □ (smaller) | Uniform or Non-uniform Dilation |
| Collimator Rotation [°] | □ | ◇ | ◇ | Rotation |
| Tube Detector Misalignment [mm] | □ | ⊡ | ⊡ | X, Y, or XY-Translation |

AUTOMATIC EXPOSURE CONTROL FOR A DIGITAL IMAGE ACQUISITION SYSTEM

BACKGROUND OF INVENTION

The present invention relates generally to x-ray imaging systems and more particularly, to exposure management in an x-ray imaging system.

Traditionally, in x-ray imaging systems, exposure management is handled by an automatic exposure control subsystem. These subsystems typically utilize a small number of predefined, fixed sensor areas that terminate the exposure when a predefined limit has been reached. The sensors areas are x-ray sensitive and usually include an ion chamber. The automatic exposure control subsystem requires dedicated hardware and calibration that is costly and difficult to maintain.

A further disadvantage of these subsystems with fixed sensors is that minimal, if any, adjustments can be made for various patient sizes, anatomical views/orientations, pathologies, or system geometries. Consequently, an optimal exposure level is not always reached, especially in cases where patient characteristics are atypical. The patient must be positioned such that the anatomy of interest is superimposed on the ion-chamber location. This is sometimes difficult and can lead to variable exposures from patient to patient and from exposure to exposure. While some portions of the image may be properly exposed, other portions are improperly exposed with some regions underexposed and other regions overexposed.

Improperly exposed images require a retake of the x-ray, which results in increased radiation dose to a patient, increased patient discomfort, increased cost to the hospital, and decreased hospital productivity.

SUMMARY OF INVENTION

It is therefore one object of the invention to predict the appropriate exposure technique parameters for an x-ray image. It is another object of the present invention to predict optimal exposure technique parameters for an x-ray image. It is still a further object of the present invention to use a low-dose preshot image and virtual ion chambers to select and control the diagnostic exposure to be imaged in a subsequent shot.

In one aspect of the invention, an automatic exposure control mechanism is provided that uses a low-dose preshot image and virtual ion chambers to select and control the diagnostic exposure to be imaged in a second shot directed to an identified region of interest. The virtual ion chambers can be configured for various patient sizes, anatomical views/orientations, pathologies, and system geometries.

According to the present invention, a virtual ion chamber or soft sensor area is defined by an overlay having divisions therein whereby all, or part, of the overlay can be selected to define a region of interest in a digital x-ray image. The region of interest may be defined by any configuration, or combination, of shapes and sizes within a given x-ray image. In one embodiment of the present invention, the region of interest is defined using a matrix of N×M simple geometric shapes.

Other objects and advantages of the present invention will become apparent upon the following detailed description and appended claims, and upon reference to the accompanying drawings.

DETAILED DESCRIPTION

Figure 1:
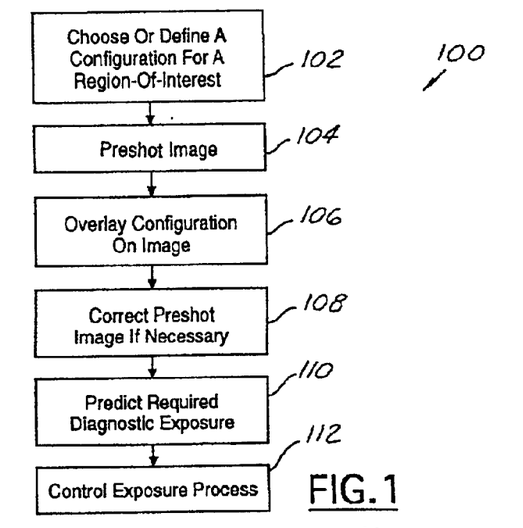
FIG. 1 is a simple flow chart of the method of the present invention.

Referring to FIG. 1, a simple flow chart 100 of the present invention is shown. A configuration for an overlay is chosen, or designed, 102 based on the desired diagnostic image, particular anatomy, and patient characteristics such as size, etc. A first, low-dose image is acquired 104, hereinafter called a preshot image, and the configuration is overlaid 104 onto the image, whereby all, or a portion of, the configuration is selected to indicate a region of interest for a subsequent diagnostic image or images.

Using the overlay configuration as a reference, the preshot image is corrected 108, if necessary, based on desired results for the subsequent diagnostic image. A prediction is made 110 based on the requirements for the diagnostic exposure and the information gathered from the preshot image. This prediction is used to control the exposure 112 of the diagnostic image in order to optimize the results for the selected region of interest. This procedure can be either manual or automatic as will described in detail later herein. Other embodiments of this invention involve variations on the N×M matrix in order to optimize the results of the diagnostic image.

Figure 2:
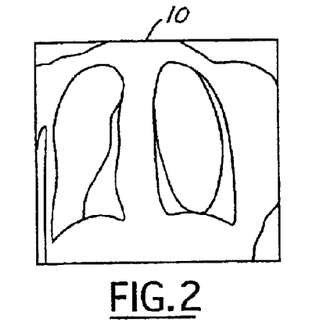
FIG. 2 is a posterior-anterior chest x-ray image having a 1×1 matrix of squares overlay.

Referring now to FIG. 2, there is shown an illustrative image, a posterior-anterior chest x-ray image 10. It should be noted that while a chest x-ray is shown in accordance with the descriptions of the present invention, the present invention is applicable to all other x-ray images. According to the present invention, regions of interest are selected from an overlay defined by a configuration of shapes and sizes within a given x-ray image. The regions of interest are preferably selected from a configuration using a matrix of N×M simple geometric shapes, such as quadrilaterals, circles, or triangles. In the simplest form, the present invention defines an array of N×M squares, where both N and M are greater than or equal to 1, N is less than or equal to the number of rows in a digital x-ray image and M is less than or equal to the number of columns in a digital x-ray image. FIG. 2 shows N=M=1.

Figure 3:
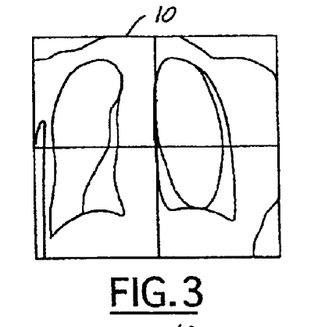
FIG. 3 is a posterior-anterior chest x-ray image having a 2×2 matrix of squares overlay.
Figure 4:
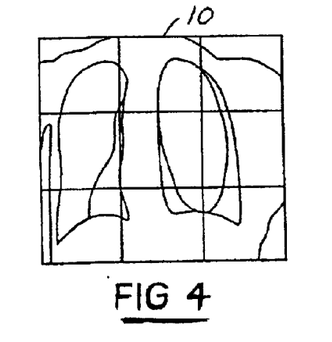
FIG. 4 is a posterior-anterior chest x-ray image having a 3×3 matrix of squares overlay.
Figure 5:
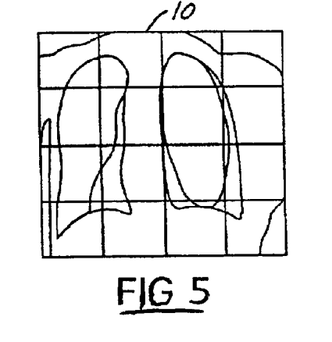
FIG. 5 is a posterior-anterior chest x-ray image having a 4×4 matrix of squares overlay.
Figure 6:
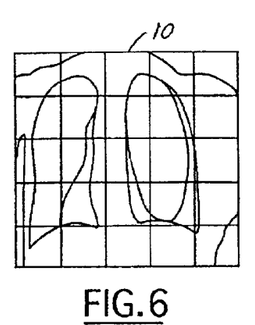
FIG. 6 is a posterior-anterior chest x-ray image having a 5×5 matrix of squares overlay.

Referring now to FIG. 3, the given x-ray image 10 is configured into a 2×2 matrix, FIG. 4 is the image 10 configured into a 3×3 matrix, FIG. 5 is the image 10 configured into a 4×4 matrix, and FIG. 6 is the image configured into a 5×5 matrix. It is apparent that the divisions shown are for example purposes only and that the variations are virtually limitless.

The divisions of the overlay configuration that are selected to define the regions of interest on the image are also called, cells, soft sensors, or virtual ion chambers. A low-dose preshot of radiation is applied to the patient, and provides a valuable frame of reference that allows control of the diagnostic exposure using information from the selected regions of interest. The parameters for the diagnostic x-ray image exposure can be optimized based on the results of the pre-shot image. For example, the overlay can be configured for various patient sizes, anatomical views/orientations, pathology, and system geometry. The exposure time, peak kilovoltage, tube current, focal spot size, collimation, source-to-imager distance (SID), and/or spectral filter can be modulated based on the results of the pre-shot image.

Figure 7:
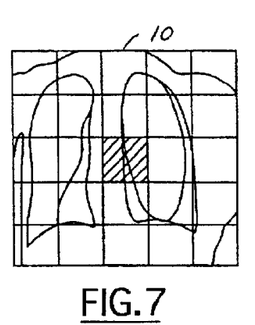
FIG. 7 is an example of a region-of-interest combination constructed from an N×M matrix where N=M=5.
Figure 8:
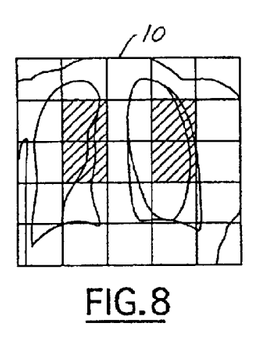
FIG. 8 is an example of a region-of-interest combination constructed from an N×M matrix where N=M=5.
Figure 9:
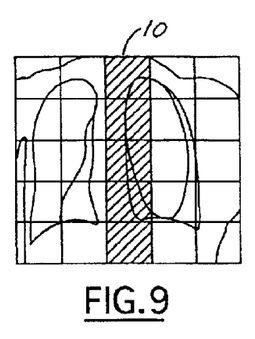
FIG. 9 is an example of a region-of-interest combination constructed from an N×M matrix where N=M=5.
Figure 10:
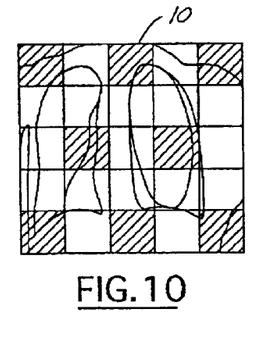
FIG. 10 is an example of a region-of-interest combination constructed from an N×M matrix where N=M=5.
Figure 11:
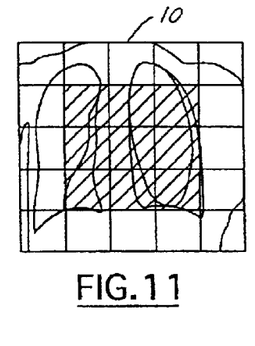
FIG. 11 is an example of a region-of-interest combination constructed from an N×M matrix where N=M=5.

Another embodiment of the present invention allows the x-ray image to focus on a particular region of interest. By selecting or deselecting divisions, or cells, in a given N×M matrix, any number of configurations is possible. FIGS. 7 through 11 provide an example of some possible region-of-interest configurations for an x-ray image 10 constructed from a 5×5 matrix. Cross-hatched areas indicate areas of interest for the determination of diagnostic image parameter settings. For example, FIG. 7 is directed to the heart, FIG. 8 is directed to each lung, and FIG. 9 is directed to the spine. It is also possible to select areas as shown in FIG. 10, where the regions of interest are many and may scattered over the entire image. FIG. 11 is yet another possible configuration. It is noted that these interpretations are customized for the illustrative chest x-ray image, but the methodology applies for any anatomical region that is imaged.

Figure 12:
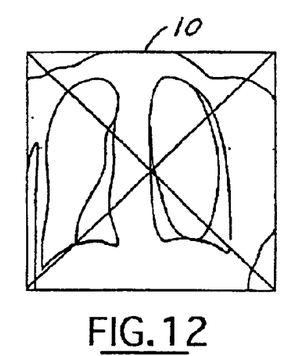
FIG. 12 shows triangle subregions in the regions of interest according to another embodiment of the present invention, where N=M=1.
Figure 13:
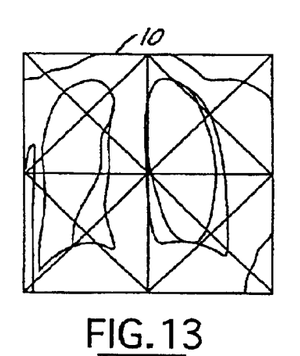
FIG. 13 shows triangle subregions in the regions of interest according to another embodiment of the present invention, where N=M=2.
Figure 14:
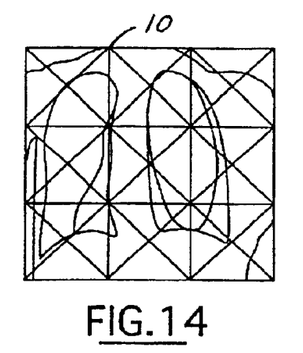
FIG. 14 shows triangle subregions in the regions of interest according to another embodiment of the present invention, where N=M=3.
Figure 15:
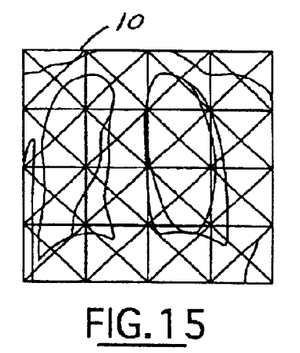
FIG. 15 shows triangle subregions in the regions of interest according to another embodiment of the present invention, where N=M=4.
Figure 16:
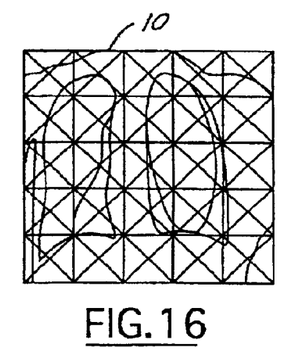
FIG. 16 shows triangle subregions in the regions of interest according to another embodiment of the present invention, where N=M=5.

In yet another embodiment of the present invention, it is possible to focus on just a portion of a particular region of interest. According to this embodiment, some or all of regions of interest are further divided into sub-regions. For example, the diagonal vertices of the regions-of-interest may be connected to form triangular sub-regions. This configuration increases the number and shapes possible for the region-of-interest combinations available for a given N×M matrix. FIG. 12 shows the triangular sub-regions for a 1×1 matrix, FIG. 13 shows the triangular sub-regions for a 2×2 matrix, FIG. 14 shows the triangular sub-regions for a 3×3 matrix, FIG. 15 shows the triangular sub-regions for a 4×4 matrix and FIG. 16 shows the triangular sub-regions for a 5×5 matrix. While only triangle sub-regions are shown, one of ordinary skill in the art is capable of implementing numerous variations of the sub-region shapes and accomplish results similar to the present invention.

Still another embodiment of the present invention allows individual weighting of each region of interest in the digital x-ray image. In this embodiment, the specific region-of-interest combinations for an N×M matrix are further extended. The weighting may be accomplished by two methods. The first, for an x-ray image containing k regions of interest, each region of interest is assigned a unity normalized weight coefficient, $w_k$, to denote the relative importance of the region.

Figure 17:
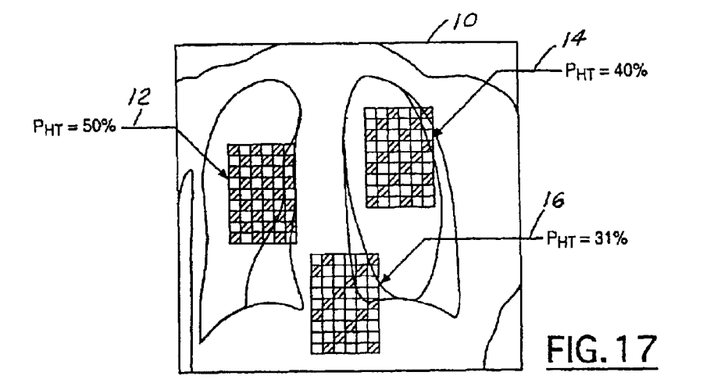
FIG. 17 is an example of ordered halftone levels used for weighting regions of interest according to the present invention.

In the alternative, a region of interest having more than one sub-region may be weighted by half-toning. Half-toning includes only a percentage, $P_{HT}$, of the pixels enclosed in the region of interest. The pixels included in a half-toned region of interest can be selected in either an ordered manner, i.e. every third pixel, or may be selected at random in a given region of interest. FIG. 17 shows an x-ray image 10 divided into three regions of interest. Each one of three regions of interest is assigned a percentage, $P_{HT}$. For example, a region 12 is assigned 50%, a region 14 is assigned 40%, and a region 16 is assigned 31%. This is indicative of the number of pixels that are to be active during statistical analysis of the preshot image.

According to the present invention, a set of default overlay configurations may be supplied with the digital x-ray system. The configurations are stored in a database as a set of image masks. The image masks can be developed based on a representative population base for each exam type. For example, a predefined image mask is available for a specific anatomical view and orientation combination, and on a typical system geometrical configuration for a specific exam type. The database also contains variations on the image masks for a number of patient sizes such as small, medium and large.

Adjustments can be made to the image masks to suit general exposure preferences ahead of time or they may be customized during the exam. Customizing the image masks involves altering settings based on the N×M matrix model. Each matrix region can be selected or deselected. Each region of interest selected from the matrix can be weighted with a unity-normalized value or by using a halftone percentage as described above. It may also be desirable to provide the function of selecting entire rows or columns in the matrix at the touch of a button.

In one embodiment of the present invention, a graphical user interface is provided wherein each matrix region can be selected or deselected, and modified as desired by an operator. The graphical user interface has a color, or grayscale, monitor and a selectivity device, such as a mouse, keypad or touch screen. Differences in the weights assigned to the various regions of interest may be represented by distinct colors or varying gray levels on the graphical user interface display. It is also desirable that the system has the capability to save customized preferences in a database for future use.

In another embodiment of the present invention, a typical exam-specific image may be used to assist an operator in fitting an overlay configuration to an application.

For example, a predefined N×M matrix is overlaid onto a typical exam-specific image and displayed for the operator to indicate approximate locations of regions of interest relative to a specific anatomical area. This type of exam-specific image may also be used to allow an operator to select a specific anatomical area in the image, such as a single lung, or a portion of a lung, in a chest image or the nasal cavity in a head image, or the heel in a foot image. The system uses an image segmentation technique to process the low-dose preshot and detect the desired anatomical area. This desired area is then used as a control region-of-interest to predict and/or optimize exposure parameters in the diagnostic (second) image acquisition.

In yet another embodiment of the present invention, automatic adjustments can be made to the regions of interest. In instances where a specific system geometry deviates from a preconfigured setting, it is possible to adjust the geometry of the regions of interest to account for any combination of source-image distance (SID), lateral and/or longitudinal tube angle, lateral and/or longitudinal detector angle, collimator field of view (FOV), collimator rotation, and tube-detector misalignment. Deviations from system geometries may occur when a patient is unusually large or small, or in instances where the specific anatomy to be imaged is not within the vicinity of its expected area.

Figure 18:
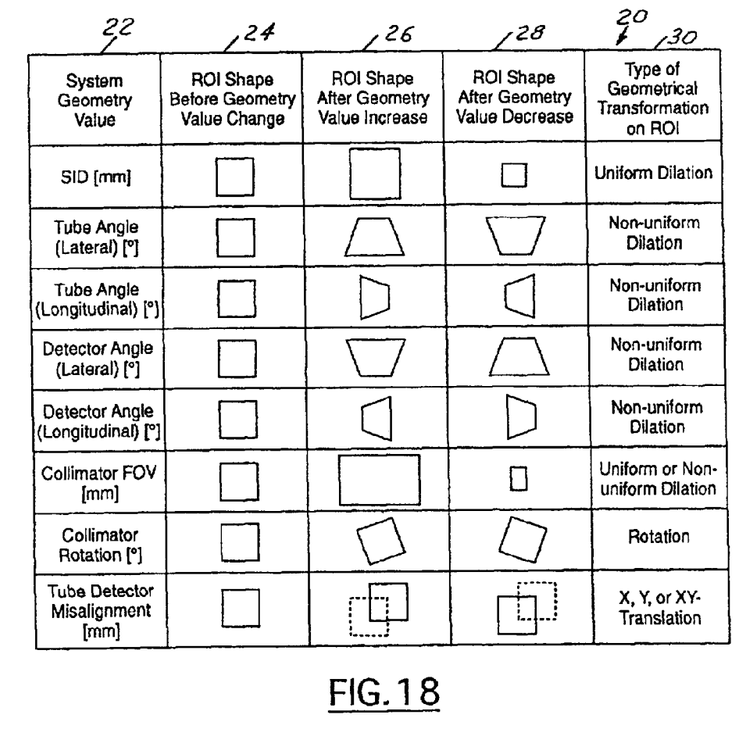
FIG. 18 is a table showing several geometrical transformations for varying system geometries according to the present invention.

FIG. 18 is a table 20 of various system geometries and how their shapes may be altered to optimize identification of the region of interest and thereby optimize image exposure according to the present invention. The table has a column of system geometry values 22, the region-of-interest shape before any change 24, the region-of-interest shape after an increase 26, the region-of-interest shape after a decrease 28, and the type of geometrical transformation 30 that occurred to alter the shape of the region of interest. By altering the geometry of the matrix cell over a specific region of interest, it is possible to encompass the entire region of interest in detail. Ultimately the selected areas are used to determine the exposure of the diagnostic image, thereby optimizing the results of the subsequent diagnostic image.

Another aspect of the present invention involves sub-region-of-interest segmentation in order to enhance the x-ray image. According to this aspect of the present invention, histogram and/or spatial image segmentation techniques can be used with any combination of the regions of interest within a region-of-interest configuration. The segmentation serves to ignore specific areas within a region of interest that contain non-value added information and highlight potential misalignment problems.

Figure 19:
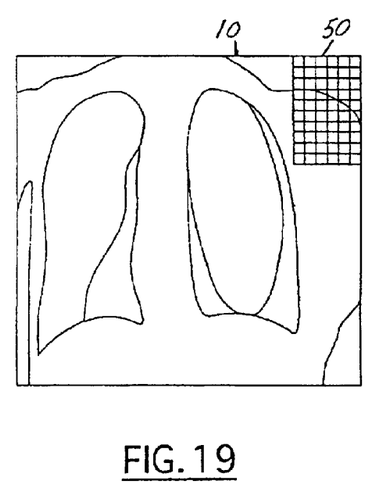
FIG. 19 is an x-ray image showing sub-region-of-interest segmentation according to the present invention.
Figure 20:
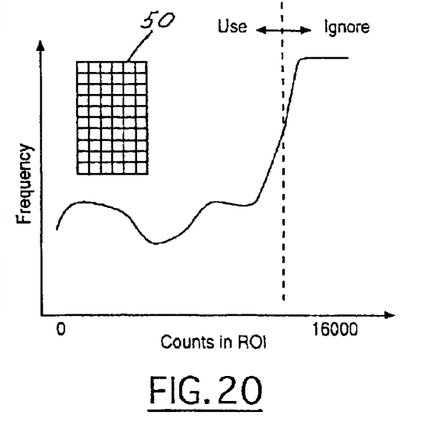
FIG. 20 is a graph of histogram segmentation techniques for excluding raw radiation which is saturating a portion of a region of interest shown in FIG. 6.

For example, histogram segmentation techniques can be used to exclude raw radiation, which may be saturating a portion of a region of interest. FIG. 19 is an example of a preshot image 10 having a grid 50 shown in the upper right-hand corner of the image 10. The upper portion of the grid outlines the saturated portion of the region of interest. FIG. 20 is a graph that indicates the portion of the region of interest that should be ignored in determining the optimum parameters for the exposure during the diagnostic imaging portion of the present invention. The histogram segmentation techniques can also be used to exclude highly attenuated radiation, as in the case of internal pacemakers and fixation devices.

Figure 21:
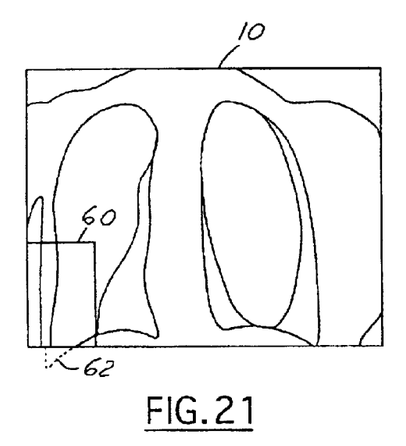
FIG. 21 is an x-ray image showing an open region, which may be indicative of a particular portion of anatomy lying outside the field of view.
Figure 22:
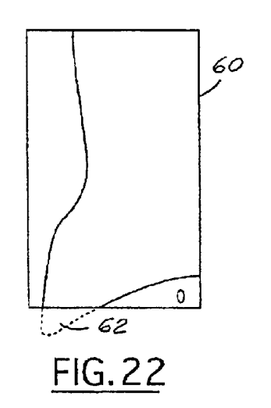
FIG. 22 is an example of a spatial segmentation technique applied according to the present invention for suggesting potential errors from open regions.

Spatial image segmentation techniques can be used to detect open regions which may indicate a particular portion of anatomy lying outside the collimated field of view. FIG. 21 shows an image 10, with a grid 60 and a dashed line marking the area 62 of the lung not captured in the preshot image 10. FIG. 22 is an outline of the grid 60 that has undergone spatial segmentation technique suggestive of anatomy outside of the field of view in the area 62. The information obtained from the preshot image segmentation technique can be relayed to the system operator as a warning or an error so that they may make necessary adjustments to optimize the diagnostic image.

It is preferable that these segmentation techniques be automated to aid the operator. However, in the instances where a patient has an extremely non-normal anatomy, an interactive mode is available in which the operator may select a manual operation to check for gross misalignments. It is noted that this interactive operation mode requires sequential image acquisitions and patient motion may affect the results.

The present invention also provides the capability to use the selected region-of-interest information in a post-acquisition image processing chain. Digital x-ray systems typically employ image processing algorithms to enhance the diagnostic image. According to the present invention, the defined regions of interest may be fed to the image processing algorithms in order to achieve specialty views of the diagnostic image. A specialty view may be a soft-tissue look, or a bone look. The region of interest information allows advanced image processing algorithms the ability to choose important x-ray image regions when processing the specialty images.

Still another capability provided by the present invention is the ability to optimize the diagnostic imaging technique. Based upon information obtained from the preshot image with a selected region of interest, the preshot dose, kVp, and maximum exposure in the image, a patient thickness can be calculated. From the patient thickness calculation, an algorithm is used to optimize the x-ray spectrum (kVp, spectral filter) to match that of the detector sensitivity while minimizing the patient dose.

Figure 23:
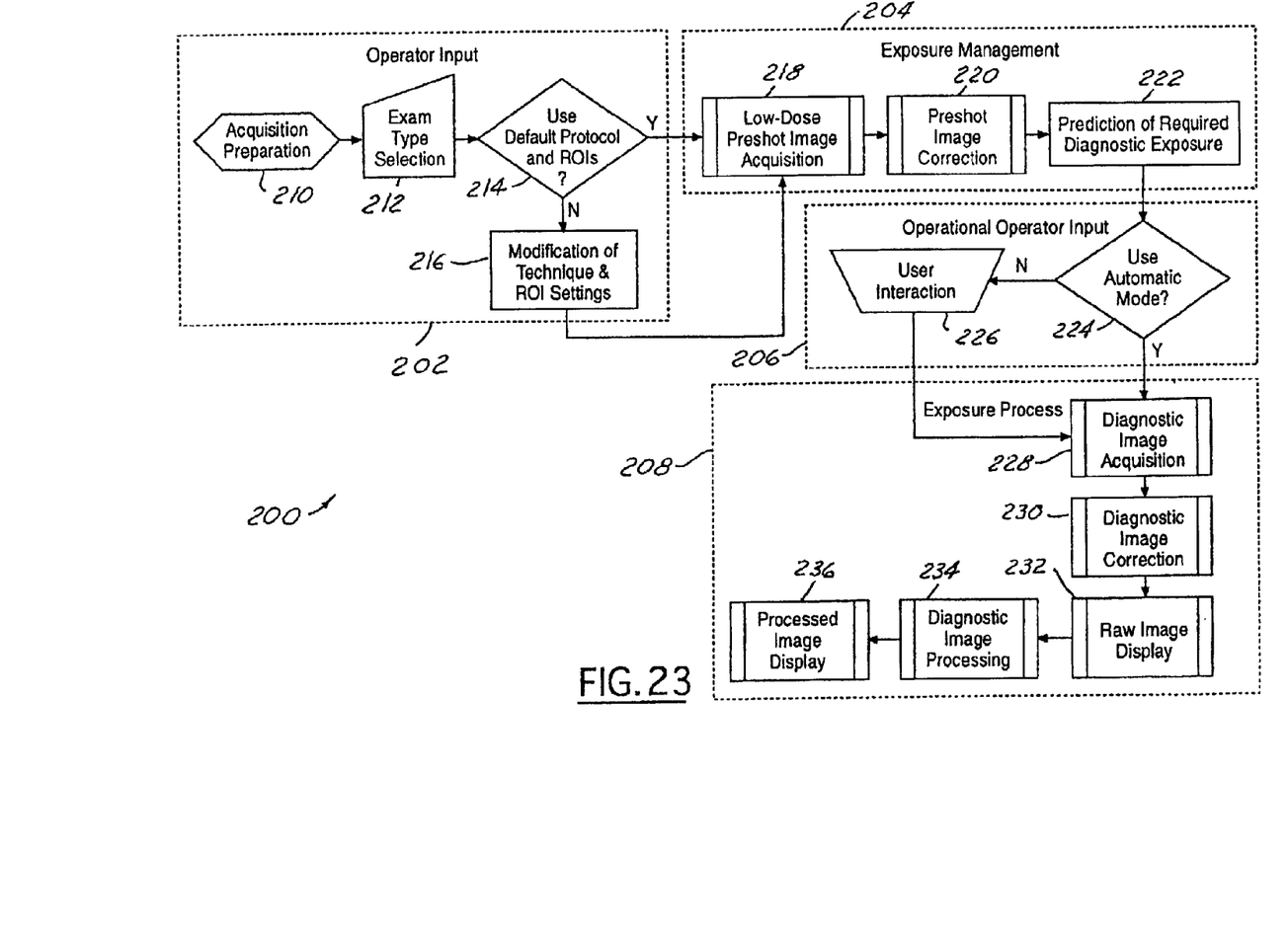
FIG. 23 is a detailed flow chart of the method of the present invention.

FIG. 23 is a flowchart 200 outlining the present invention in many of its embodiments. The flowchart can be divided into four major areas, operator input 202, exposure management 204, optional operator input 206, and exposure process 208. These areas are all interrelated and allow some sort of operator input at each stage.

Operator input 202 involves preparation 210 for the acquisition of the diagnostic image. The type of exam is selected 212 from a stored database. The operator then chooses whether to use a default protocol and region-of-interest configuration 214 or to customize 216 a protocol for a specific application. The exposure management 204 section follows.

During the exposure management 204 portion of the present invention, a low-dose preshot image is acquired 218, the preshot image is then corrected 220 as necessary. Using information gathered from the preshot image acquisition, a prediction can be made as to the required exposure 222 for a subsequent diagnostic image or sequence of diagnostic images. As an option, the operator can choose an automatic mode 224 or an interactive mode 226 in which the region of interest can be selected, moved, altered, etc. according to the embodiments described above.

The exposure process 208 itself follows. The diagnostic images are acquired 228 and any corrections 230 that are necessary can be made to the image. The raw images are displayed 232 for the operator to view. At this point, it is possible for the operator to manipulate the images through image processing 234, for example, to highlight tissue as opposed to bone, etc., and then display 236 the processed image.

The present invention provides a method of defining, or identifying, regions of interest for exposure management in a digital x-ray imaging system, and especially in the case of multiple consecutive image acquisitions. According to the most basic embodiment of the present invention, simple geometric shapes arranged in a matrix configuration are used to aid an operator in identifying a region of interest for a diagnostic x-ray image. Each region of interest is selectable from a low-dose preshot image and may be corrected, or processed, in order to enhance the results of the diagnostic image. The processing of the preshot image allows the system to automatically make predictions for the diagnostic image exposure requirements, thereby avoiding unnecessary multiple images.

The present invention also provides a database of standard configurations that are made available to the operator based on exam type, patient configuration, etc. An interactive user interface allows the operator to use a predetermined configuration, modify an existing configuration, or design a completely new configuration. It is also possible to make any modifications ahead of the exam, or they may be made as needed during the exam.

The ability to select and deselect regions of interest, can be further applied to image processing after the diagnostic image has been acquired. This allows the operator to optimize the results of digital image acquisition thereby eliminating much patient discomfort, any unnecessary exposure to radiation, and keeping hospital operating costs low.

While the invention has been described in connection with one or more embodiments, it should be understood that the invention is not limited to those embodiments. On the contrary, the invention is intended to cover all alternatives, modifications, and equivalents, as may be included within the spirit and scope of the appended claims.

What is claimed is:

1. A method for identifying a region of interest for a digital x-ray system, said method comprising the steps of:
   obtaining a low-dose preshot image;
   overlaying said preshot image with a predefined configuration having at least one division;
   selecting at least one division from said predefined configuration to identify a region of interest for at least one subsequent diagnostic image;
   determining exposure characteristics for said subsequent diagnostic image based on said identified region of interest;
   obtaining at least one diagnostic image using said determined exposure characteristics.

2. The method as claimed in claim 1 wherein said preshot image is a prior diagnostic image.

3. The method as claimed in claim 1 wherein said predefined configuration is a simple N×M matrix structure having simple geometric shapes for each cell of said matrix.

4. The method as claimed in claim 3 wherein said simple geometric shapes are squares.

5. The method as claimed in claim 4 wherein said squares are further divided in triangular subregions.

6. The method as claimed in claim 1 wherein said step of selecting at least one division further comprises the step of weighting said region of interest for exposure control management.

7. The method as claimed in claim 6 wherein said weighting is accomplished by way of a relative unity-normalized weighting coefficient.

8. The method as claimed in claim 6 wherein said weighting is accomplished by way of applying variable half-tone percentages to said region of interest.

9. The method as claimed in claim 1 further comprising the steps of modifying said predefined configuration according to exam specific characteristics.

10. The method as claimed in claim 9 further comprising the step of adjusting said predefined configuration based on a patient size.

11. The method as claimed in claim 1 wherein said step of overlaying a predefined configuration further comprises choosing a predefined configuration for a specific exam type.

12. The method as claimed in claim 11 wherein said specific exam type is anatomy specific.

13. The method as claimed in claim 11 wherein said specific exam type is orientation specific.

14. The method as claimed in claim 1 wherein said step of overlaying a predefined configuration further comprises choosing an exam specific configuration from a database of predefined image masks.

15. The method as claimed in claim 14 wherein said database of predefined image masks contains image masks derived from a representative population.

16. The method as claimed in claim 9 further comprising the step of saving a modified configuration.

17. The method as claimed in claim 1 wherein said step of selecting said at least one division further comprises the step of adjusting a geometry of said division to further define said region of interest.

18. The method as claimed in claim 17 wherein said step of adjusting a geometry further comprises adjusting a size of said division.

19. The method as claimed in claim 17 wherein said step of adjusting a geometry further comprises adjusting a lateral tube angle of said division.

20. The method as claimed in claim 17 wherein said step of adjusting a geometry further comprises adjusting a longitudinal tube angle of said division.

21. The method as claimed in claim 17 wherein said step of adjusting a geometry further comprises adjusting a lateral detector angle of said division.

22. The method as claimed in claim 17 wherein said step of adjusting a geometry further comprises adjusting a longitudinal detector angle of said division.

23. The method as claimed in claim 17 wherein said step of adjusting a geometry further comprises adjusting a collimator field of view for said division.

24. The method as claimed in claim 17 wherein said step of adjusting a geometry further comprises adjusting a collimator rotation for said division.

25. The method as claimed in claim 17 wherein said step of adjusting a geometry further comprises adjusting a tube detector misalignment for said division.

26. The method as claimed in claim 1 further comprising the steps of:
   dividing said identified region of interest into segments;
   applying an algorithm to identify areas of said region of interest that contain non-value added information;
   using histogram techniques to exclude areas of non-value added information during said step of determination of exposure characteristics.

27. The method as claimed in claim 26 further comprising the steps of:

dividing said identified region of interest into segments;

applying an algorithm to identify areas of said region of interest that contain non-value added information;

using spatial image segmentation to identify open regions indicating a particular part of the anatomy is truncated from a field of view;

providing a warning to indicate truncated anatomy exists;

making necessary adjustments to include truncated anatomy before obtaining said at least one diagnostic image.

28. The method as claimed in claim 6 further comprising the steps of:

communicating said selected division and weighting of said division to a processor;

processing said diagnostic image using said region of interest information to enhance an output of said at least one diagnostic image.

29. The method as claimed in claim 1 further comprising the steps of:

acquiring multiple images;

modifying said predetermined configuration between multiple image acquisitions.

30. A method of exposure management in a digital x-ray system, said method comprising the steps of:

preparing for acquisition of at least one diagnostic image;

selecting an exam type from a database;

selecting a default region-of-interest configuration for said selected exam type;

modifying said default region-of-interest configuration as needed;

acquiring a preshot image using a low dose of radiation;

correcting said preshot image by selecting divisions in said region-of-interest configuration;

predicting a required exposure for at least one diagnostic image from said corrected preshot image; and acquiring at least one diagnostic image.

31. The method as claimed in claim 30 further comprising the step of selecting between an automatic mode and an interactive mode for said step of correcting said preshot image.

32. The method as claimed 30 further comprising the steps of:

correcting said at least one diagnostic image using information from said preshot image;

displaying said at least one diagnostic image;

processing said at least one diagnostic image using image processing techniques to enhance a desired result for said at least one diagnostic image; and displaying said processed diagnostic image.

* * * * *